(12) United States Patent
Imoto

(10) Patent No.: US 7,216,527 B2
(45) Date of Patent: May 15, 2007

(54) GAS DETECTION DEVICE

(75) Inventor: Tsutomu Imoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 207 days.

(21) Appl. No.: 10/515,280

(22) PCT Filed: May 23, 2003

(86) PCT No.: PCT/JP03/06472

§ 371 (c)(1),
(2), (4) Date: Nov. 22, 2004

(87) PCT Pub. No.: WO03/106975

PCT Pub. Date: Dec. 24, 2003

(65) Prior Publication Data

US 2005/0252273 A1    Nov. 17, 2005

(30) Foreign Application Priority Data

May 28, 2002  (JP) ............................ 2002-153862
Apr. 23, 2003  (JP) ............................ 2003-117715

(51) Int. Cl.
    *G01N 7/00*    (2006.01)
(52) U.S. Cl. ................... 73/23.34; 73/1.06; 73/23.2
(58) Field of Classification Search ............... 73/23.34, 73/23.41, 23.2, 31.01, 31.02
    See application file for complete search history.

(56) References Cited

U.S. PATENT DOCUMENTS 3,446,600 A * 5/1969 Eckstein et al. ............... 422/88
5,090,232 A * 2/1992 Wakabayashi et al. ..... 73/23.34
6,459,955 B1 * 10/2002 Bartsch et al. .............. 700/245
6,708,081 B2 * 3/2004 Yoshida ....................... 700/245

2003/0093187 A1 * 5/2003 Walker .......................... 701/1

FOREIGN PATENT DOCUMENTS

| JP | 61-24932 | 7/1986 |
| JP | 2-45445 | 3/1990 |
| JP | 2-45445 U | * 3/1990 |
| JP | 5-72094 | 3/1993 |

(Continued)

*Primary Examiner*—Hezron Williams
*Assistant Examiner*—Ryan Christensen
(74) *Attorney, Agent, or Firm*—Oblon, Spivak, McClelland, Maier & Neustadt, P.C.

(57) ABSTRACT

A gas detector capable of accurately measuring particular components (odors or the like) contained in an ambient gas to be measured, being compact, and capable of being easily formed to be portable, or producing low noise and capable of being small-sized. Having zero gas cylinder (9) as a supplying unit of a zero gas and component parts disposed within its enclosure (2) and using syringe (3) as a gas intake/exhaust unit, it alternately introduces a test gas, i.e., an ambient gas taken in from outside enclosure (2) through piping (12a), and the zero gas supplied from zero gas cylinder (9) into sensor unit (7) and measures the test gas, while having operation of each unit controlled by data processor (11). Thus, accurate measurement of the test gas is achieved by relatively comparing results of measurement on the gases at each measurement. In addition, gas detector (1) can be moved to a spot where measurement is to be made to have the test gas there measured. Further, by use of a cylinder mechanism producing low noise, the detector can quantify gas intake/exhaust and can be made small in size.

10 Claims, 10 Drawing Sheets

FOREIGN PATENT DOCUMENTS

| | | |
|---|---|---|
| JP | 6-198586 | 7/1994 |
| JP | 9-250979 | 11/1997 |
| JP | 9-304244 | 11/1997 |
| JP | 11-83702 | 3/1999 |
| JP | 2000-155107 | 6/2000 |
| JP | 2001-41016 * | 2/2001 |
| JP | 2001-41916 | 2/2001 |
| JP | 2002-36158 | 2/2002 |

* cited by examiner

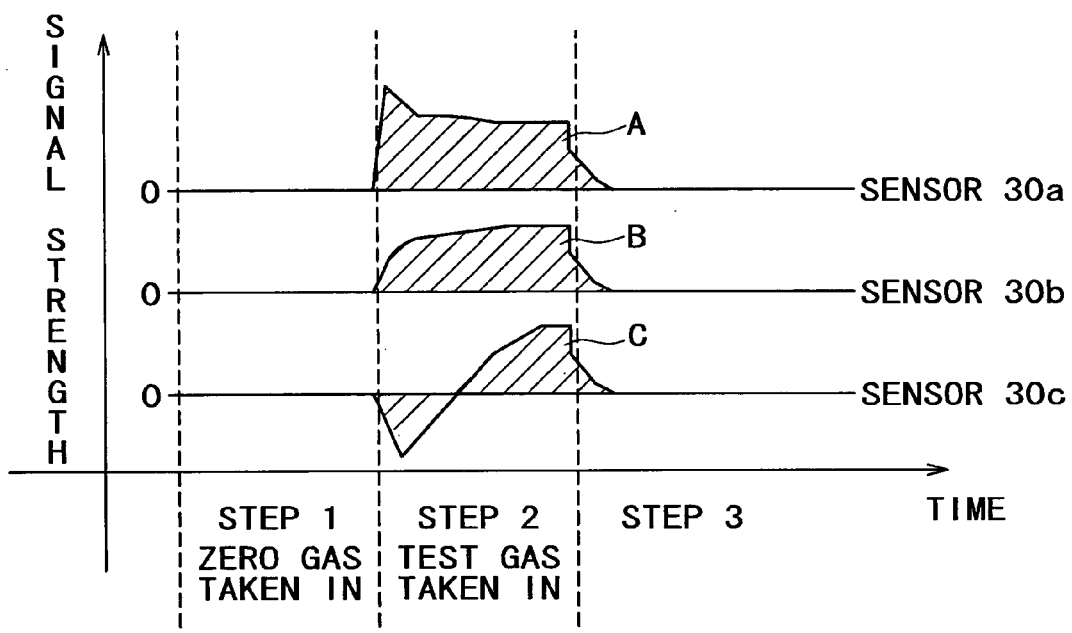
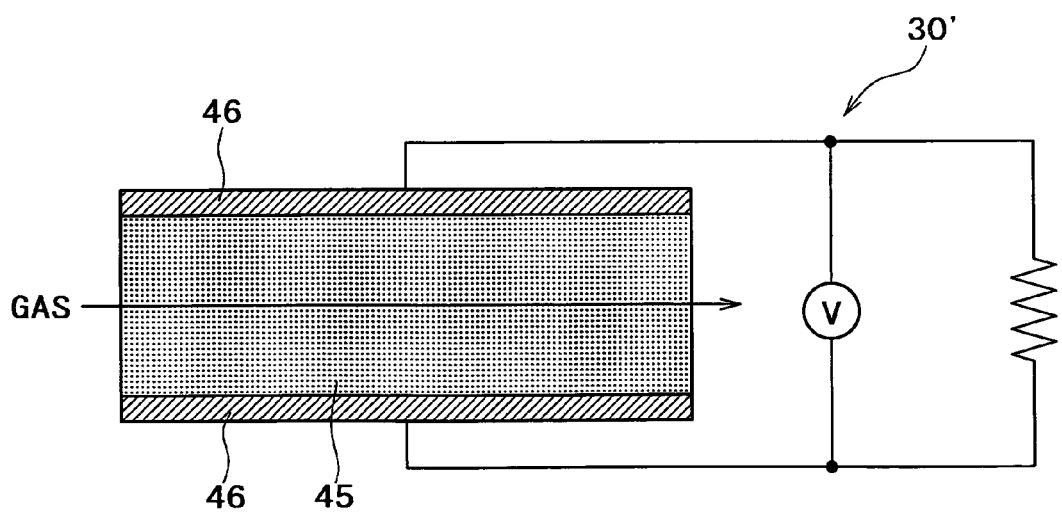

TO SENSOR MEASURING CIRCUIT

GAS DETECTION DEVICE

TECHNICAL FIELD

The present invention relates to a portable gas detector capable of detecting a particular component in an atmosphere and identifying, for example, an odor.

BACKGROUND ART

FIG. 14 is a block diagram of a conventional odor identifier 31. In FIG. 14, gas in the atmosphere is taken in through intake port 36, allowed to flow through sensor 34 installed in the path of piping 38, sent to exhaust pole 37 by pump 33 to be returned to the original atmosphere. At this time, an electric signal corresponding to the kind of the odor borne by the gas taken in is derived from sensor 34 and identification and concentration measurement of the odor are performed in data processor 35.

FIG. 15 is a schematic outside view of conventional odor identifier 31 configured as described above. Within main body 32, there are incorporated sensor 34, data processor 35, pump 33, and the like shown in FIG. 14. An ambient gas taken in as zero gas (reference gas) 42 and test gas (gas for test) 43 contained in test gas container 44 are alternately introduced into sensor 34 through intake port 36 at the top end of a sample probe projected from main body 32 and, thus, the kind of the odor, concentration, and the like of the test gas are measured.

However, with repetition of the measurement, the odorous component attaches sensor 34 and hence the zero level of sensor 34 gradually changes from its initial state and an accurate measurement becomes unattainable. Therefore, the zero gas is alternately taken in every time so that the zero level of sensor 34 is adjusted. The odor identifier is put into operation by manipulation of measurement start button 41 and the measured value is displayed on meter 40.

In conventional odor identifier 31, odor analysis is performed by detection of physical change or chemical change produced by adsorption of molecules of the odor component by the sensor material.

In a quartz crystal microbalance (QCM), for example, different kinds of adsorbents are applied to the surface of the quartz crystal and changes in mass produced by adsorption of the odor molecule by the adsorbents are detected by changes in number of vibration of the quartz oscillator. Since the kinds of chemical substances that are easily adsorbed differ with characteristics of the odor molecules, such as strength of polarity, the kind and quantity of the odor molecules constituting the odors can be estimated by measuring how much of change in the mass is produced in which of the adsorbents.

Adsorption of odor molecules can be detected not only by change in mass, but also by change in electric resistance, change in absorption wavelength of light, and the like, and there are proposed various sensors of such types. For example, such a sensor is put into practice that makes use of change in electric resistance when an odor molecule is adsorbed by a conductive polymer or by a composite material of an insulating polymer with conductive particles dispersed therein.

However, when sensor materials adsorbing odor molecules are used, it is unavoidable that the odor molecules remain on the surface of the sensor material or that a highly active molecule contained in the gas combines with the sensor material to thereby cause the quality of the sensor material to be changed.

Since, in such sensors, the sensor characteristic is changed by the history of its use, a relative difference, not an absolute value, of the sensor signal (the number of vibration for a quartz oscillator system, the electric resistance for a chemo resistor type, the absorption wavelength of light for an optical system, and so on) is mainly utilized. Since such a relative difference is measured as the difference in strength between signals from a reference gas (zero gas) not including the odor and from a gas for test (test gas), it is required to measure both the signals of the zero gas and the test gas in order to identify the odor.

Therefore, in the case of odor identifier 31 shown in FIG. 15, the odor is identified following such steps as, first, to measure the outside air, such as the room air, as the zero gas, and then, by inserting intake port 36 into container 44 such as a flask containing a sample, to measure the odor of the sample.

In this way, when identifying an odor with use of an odor identifier, it is required to measure both the test gas and the zero gas. In the case where the odor of a substance contained in a container is to be identified with use of odor identifier 31 shown in FIG. 15, the gas obtained by inserting intake port 36 into the container is used as the test gas and the gas obtained when intake port 36 is placed outside the container is used as the zero gas, and thus relative difference between the sensor signals is measured and the odor inside the container can be identified.

However, when an odor widely floating in the atmosphere surrounding the odor identifier is to be identified, it is impossible to take in the zero gas from the surroundings, and hence there has been a problem that the odor widely floating in the environment cannot be identified.

As an apparatus of the described type, there is disclosed an odor identifier with use of a zero gas container in Japanese Laid-open Patent Publication No. Hei 9-250979. However, this is not what aims at identification of an atmospheric odor. It is configured to take in the test gas, as well as the zero gas, from a container connected to the apparatus and it is not designed to be portable for identifying an atmospheric odor. Further, since the layout of the piping for making switchover between the zero gas and test gas is complicated and the switchover is troublesome, it is considered difficult to arrange this apparatus in a size suited for carrying.

Further, in Japanese Laid-open Patent Publication No. Hei 9-304244 is disclosed an odor identifier making it possible to identify an atmospheric odor by purifying the outside air and using the same as the zero gas. In this case, although consideration has been given to portability and identification of the atmospheric odor, the mechanism is complicated and switching is troublesome because measurement and purification of the outside gas is performed through valve changeover. Therefore, it is considered difficult to configure the apparatus in such a size that is capable of being incorporated into a small-sized household robot.

Further, in Japanese Laid-open Patent Publication No. 2000-155107, there is disclosed an odor identifier using a zero gas container in combination therewith. In this apparatus, identification or quantification of a sample gas is performed on the basis of a detected signal from the sample gas and a detected signal from the zero gas. However, the zero gas container is not of a built-in type and gas intake and exhaust is performed by use of a pump. Hence, variations are produced in the intake and exhaust quantities. Further, it produces noise and not made to be portable with the objective of being carried to measure an atmospheric odor. Further, since it is complicated in structure and requires valve change-over, it is considered that its operability is not good and configuring it in a portable size is difficult.

Further, in the conventional odor identifiers, there are such that use a fan or a diaphragm pump for gas intake. These are large in outer size and high in noise level when operated. Hence, these are not necessarily considered suited for portable use or incorporated use in a small-sized robot to be used in houses where quietness is desired.

Accordingly, an object of the present invention is to provide a gas detector capable of accurately measuring particular components (odors and the like) contained in an ambient gas which is desired to be measured and, further, being compact and capable of being easily arranged into a portable one, or producing low noise and capable of being small-sized.

DISCLOSURE OF THE INVENTION

More specifically, the present invention relates to a gas detector characterized, in a gas detector alternately introducing a reference gas and a test gas into a sensor within an enclosure for detecting a particular component in the test gas, by that a source of supply of the reference gas is installed within the enclosure incorporating the sensor therein and that the test gas is taken in from outside the enclosure (hereinafter referred to as "first gas detector of the present invention").

According to the first gas detector of the present invention, the source of supply of the reference gas is installed within the enclosure and the test gas is taken in from outside the enclosure, and hence it is made possible to measure the ambient gas by introducing, as the test gas, the ambient gas of a region where measurement is to be made from outside the enclosure, and to introduce alternately the test gas or the reference gas into the sensor incorporated in the enclosure and relatively compare the results of measurement of the gases at each measurement to thereby make accurate measurement of the test gas. Since, at this time, the reference gas is introduced from the source of supply of the reference gas installed within the enclosure, the whole of the detector can be made more compact than when the source of supply of the reference gas is disposed outside. In addition, it is made easy to arrange such that the detector itself including the source of supply of the reference gas may be moved to any place where measurement is to be made.

Further, the present invention relates to a gas detector, in a gas detector alternately introducing a reference gas and a test gas into a sensor within an enclosure for detecting a particular component in the test gas, characterized by that a source of supply of the reference gas is connected with the sensor and the test gas is taken in from outside the enclosure, and that the reference gas or the test gas is introduced into the sensor by reciprocating motion of a piston in a cylinder mechanism, for intake and exhaust of gases by expansion and contraction of its inner volume, formed of the piston and the cylinder in combination (hereinafter, referred to as "second gas detector of the present invention").

According to the second gas detector of the present invention, the reference gas from the source of supply of the reference gas or the test gas from outside the enclosure is introduced into the sensor by reciprocating motion of the piston of the cylinder mechanism. Accordingly, an ambient gas can be measured by taking in the ambient gas from outside the enclosure as the test gas, and further, the test gas and the reference gas from the source of supply of the reference gas can be alternately introduced into the sensor, so that the results of measurement on these gases are relatively compared at each measurement, and thereby accurate measurement of the test gas can be made. Further, since these gases are taken in or exhausted by reciprocating motion of the piston in the cylinder, the intake and exhaust of gases can be quantified and, in addition, a low-noise and small-sized gas detector can be provided.

Further, the present invention also provides a gas detector characterized, in a gas detector alternately introducing a reference gas and a test gas into a sensor for detecting a component contained in the test gas, by that the sensor and the source of supply of the reference gas are integrated in one body (hereinafter referred to as "third gas detector of the present invention").

According to the third gas detector of the present invention, the sensor and the source of supply of the reference gas are integrated in one body, and therefore, merits equivalent to those obtained by the first gas detector of the present invention can be obtained and, in addition, it can be arranged to be portable (specifically, to be mountable on a mobile robot) with the sensor and the source of supply of the reference gas integrated in one body.

BRIEF DESCRIPTION OF THE DRAWINGS

FIG. 2 is a graph showing a principle drawing of signal waveforms detected by the same first embodiment.

FIG. 3 is a principle drawing showing structure and function of a sensor in the gas detector according to the same first embodiment.

FIG. 5A and FIG. 5B are drawings showing the constitution of the sensor unit of the same gas detector, in which FIG. 5A is a schematic diagram and FIG. 5B is a sectional view taken along the line b—b of FIG. 5A.

BEST MODES FOR CARRYING OUT THE INVENTION

Figure 1:
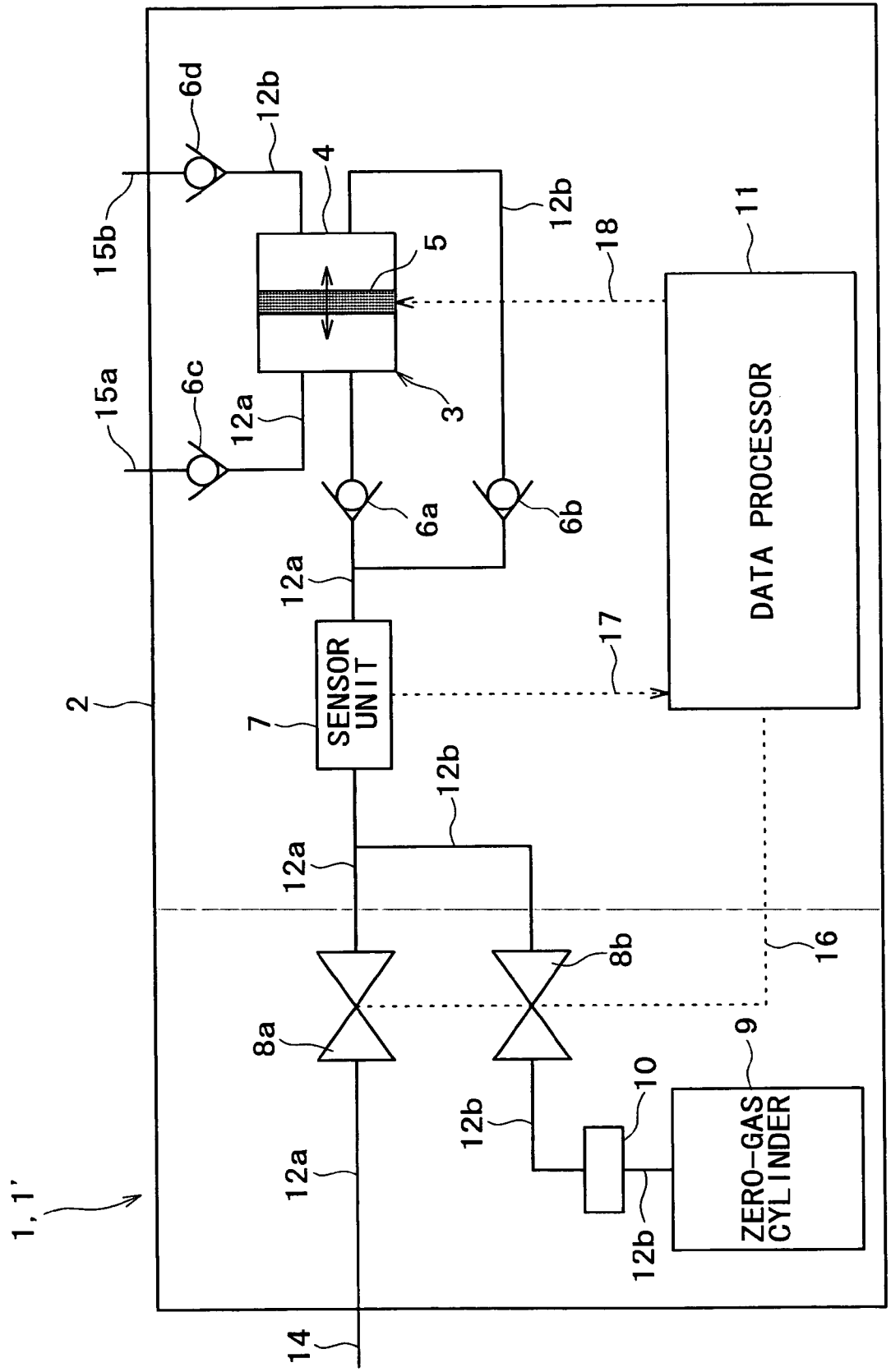
FIG. 1 is a schematic block diagram of a gas detector according to a first embodiment of the present invention.

A preferred embodiment of the present invention will be described below.

In the first, second, and third gas detectors of the present invention mentioned above, it is desired that the enclosure be portable and the test gas be the ambient gas outside the enclosure because it is thereby made possible to measure the ambient gas at a spot.

In this case, it is preferred that the source of supply of the zero gas is a container containing the zero gas because it is thereby made easy to incorporate the enclosure into the apparatus and it makes the whole of the apparatus compact enabling it to be moved easily.

It is especially preferred that the sensor and the source of the zero gas are incorporated for example in a stand-alone robotic apparatus capable of operation in an autonomous manner, or the sensor and the source of supply of the zero gas are housed in one enclosure and the test gas is supplied from the surroundings of the robotic apparatus, that is, from outside the enclosure, for example.

Further, it is preferred that the apparatus is provided with an intake or exhaust mechanism capable of taking in or exhausting gas by expansion or contraction of its inner volume, a path of the zero gas or the test gas communicating with the intake or exhaust mechanism, a source of supply of the zero gas for determining the zero level in the detection on the test gas, the sensor for measuring the zero gas and the test gas, and a controller performing at least one of processing of the output data from the sensor and controlling of operation of each unit, and that it is adapted therein such that the test gas or the zero gas is supplied to the sensor by the taking in or exhausting operation of the intake or exhaust mechanism and the particular component in the test gas is identified based on the strength of a measured signal.

Further, such an arrangement to have the reference gas or the test gas introduced into the sensor by reciprocating motion of a piston of a cylinder mechanism formed of the piston and the cylinder in combination is preferred because the intake and exhaust can be quantified, and it is made easy to configure the detector so as to produce low noise and to be small in size.

In this case, it is preferred, when a gas is taken in, that a one-way valve introducing the gas only in one direction from the sensor to the cylinder mechanism is used and, when the gas is exhausted, that a one-way valve allowing the gas to flow only in one direction from the cylinder mechanism to an exhaust port is used, and that the one-way valves for taking in the gases are connected between the sensor and two chambers of the cylinder mechanism partitioned by the piston.

More specifically, one side of the two chambers of the cylinder mechanism is connected by a one-way valve each with the sensor and the exhaust port, the other side is connected by a one-way valve each with the sensor and the exhaust port, each of the one-way valves connecting the sensor with the cylinder mechanism opens and closes to cause the gas to flow only from the sensor to the cylinder mechanism, and each of the one-way valves connecting the cylinder mechanism with the exhaust ports opens and closes to cause the gas to flow only from the cylinder mechanism to the exhaust ports, and thereby gasses can be ceaselessly taken into the sensor by a single cylinder mechanism.

In this case, it is preferred that there are provided an intake port for taking in the test gas from outside the enclosure to its interior, a first valve disposed between the port and the sensor, and a second valve disposed between the source of supply of the reference gas and the sensor, and that, when the piston moves in one direction, the first valve is opened and the test gas is taken into the sensor and, when the piston moves in opposite direction, the second valve is opened and the reference gas is taken into the sensor, so that the reference gas and the test gas are alternately and ceaselessly sent into the sensor by motion of a single cylinder mechanism.

In the gas detector, it may be arranged such that the source of supply of the reference gas is a purifying unit of the test gas and the test gas after the detection is purified by the purifying unit and thereafter reused as the reference gas. Thereby, a merit is obtained that a source of supply generating and supplying the reference gas can be built in without the need for a reference gas storage container.

Further, when purification is not attained by one time of purifying processing, the test gas gone through the detection and, then, passed through the purifying unit for being purified may be passed through the purifying unit again to be turned into the reference gas.

In this case, it is preferred that a container is provided for temporarily storing the test gas passed through the purifying unit and that the test gas is introduced into the sensor again.

More specifically, it is preferred, when the test gas is taken in from the gas intake port to the cylinder mechanism, the gas gone through the detection in the sensor is purified by the purifying unit and stored in the cylinder mechanism temporarily, and when it is exhausted from the cylinder mechanism, the gas is passed through the purifying unit again to be purified and turned into the reference gas, and thereafter, this reference gas is introduced into the sensor.

Further, it is preferred that the purifying unit is a deodorizing or dehydrating unit and the test gas introduced therein is deodorized or dehydrated or subjected to both of the processing to be turned into the reference gas.

By the installation in the enclosure of the container containing the reference gas or the installation in the enclosure of the purifying unit generating the reference gas as the source of supply of the reference gas, as described above, a portable test gas apparatus suited for odor identification can be configured.

Preferred embodiments of the above-described first, second, and third gas detectors will be described below concretely with reference to the accompanying drawings.

First Embodiment

This gas detector is such that detects a particular component (odor) contained in a gas for testing (hereinafter, it may sometimes be called "test gas"), its quantity, its concentration, and others. The difference in the basic configuration between first gas detector 1 and second gas detector 1' is that first gas detector 1 is specified by having the source of supply of a gas for reference (hereinafter, it may sometimes be called "zero gas") installed in the enclosure and second gas detector 1' is specified by having a cylinder mechanism provided as the gas intake/exhaust mechanism.

Accordingly, in the following description (including description of other embodiments to be described later), if there is made no remark as to whether it relates to the first or the second gas detector, the description is applicable to both thereof in common. Incidentally, the drawings in the following description will also be used as drawings applicable to both in common.

First gas detector 1 in its schematic configuration as shown in FIG. 1 has, within enclosure 2, compressed-gas cylinder 9 as the source of supply of zero gas, sensor unit 7 for gas detection, and data processor 11 for data processing and controlling operation of each part.

As the gas intake/exhaust mechanism, cylinder mechanism (syringe) 3 formed of a combination of a piston and a cylinder, for example, is internally provided. The outside air taken in through intake port 14 as the test gas and the zero gas supplied from compressed-gas cylinder 9 through regulator 10 are passed through piping 12a or 12b and supplied to sensor unit 7 for measurement by opening and closing of first valve 8a and second valve 8b. The gases gone through the measurement is taken into cylinder mechanism 3 through one-way valve 6a or 6b and exhausted through one-way valve 6c or 6d. Operation of each part is controlled by data processor 11. Therein, syringe 3 as the gas intake/exhaust mechanism may be the essential component.

Thus, first gas detector 1 is enabled to measure the outside air, widely floating in the surroundings, introduced as the test gas and the zero gas internally supplied, compare relatively the results of measurement of the sensor signals with each other at each time of the measurement, and make accurate measurement of the difference constantly, and therefore it is achieved with simplicity to identify the environmental odor. Accordingly, the conventional need for valve change-over can be eliminated and, hence, a small-sized odor identifier providing good operability, simplified in structure, suited for carrying and built-in arrangement can be realized and, in addition, the apparatus itself can be moved to any desired place.

Second gas detector 1' is configured as shown in FIG. 1 by having sensor unit 7, data processor 11 for data processing and controlling operation of each part, and cylinder mechanism (syringe) 3 arranged within enclosure 2.

The zero gas is supplied for example from zero-gas cylinder 9 installed in the enclosure and the outside air as the test gas is introduced through intake port 14. By operation of cylinder mechanism 3, these gases, i.e., the outside air introduced through intake port 14 and the zero gas supplied from compressed-gas cylinder 9 through regulator 10 are allowed to flow through piping 12a or 12b and supplied to sensor unit 7 for measurement therein by opening and closing of first and second valves 8a and 8b. The gas gone through the measurement is introduced into cylinder mechanism 3 through one-way valve 6a or 6b and exhausted through one-way valve 6c or 6d. Operation of each part is controlled by data processor 11. Incidentally, the internal installation of zero-gas cylinder 9 as the source of zero gas may be the essential component of the configuration.

Thus, by the use of syringe (or, it may be a bellows pump) 3, second gas detector 1' is enabled to reduce noises produced during its operation and, by introducing the ambient gas from outside enclosure 2 and alternately introducing the same and the zero gas into the sensor for measurement, the results of measurement can be subjected to relative comparison at each measurement to thereby attain accurate measurement. In addition, it eliminates the conventional need for valve change-over and is simplified in structure, a small-sized odor identifier providing good operability and suited for carrying and built-in arrangement can be configured and it is made possible to move the apparatus itself to anywhere where measurement is to be made.

In FIG. 1, the sensor to be used may be the same as that in conventional use. As intake/exhaust unit, syringe 3 provided with an intake port and an exhaust port provided on both sides thereof is used. Between intake port 14 and sensor unit 7, there is provided first valve 8a, while between zero-gas cylinder 9 and sensor unit 7, there is provided second valve 8b. First valve 8a and second valve 8b are valves for alternate switching between the zero gas from zero-gas cylinder 9 and the test gas from intake port 14, and opening and closing of the same is controlled by control signal 16 from data processor 11, hence there is no need for valve change-over.

Zero-gas cylinder 9 is a cylinder filled with dry air, nitrogen, and the like. When the zero gas within the cylinder is used up, the cylinder may be replaced with a new cylinder or the cylinder may be refilled with the gas. Regulator 10 is for adjusting the pressure of the zero gas impressed on the side of second valve 8b. The test gas may also be a gas sampled at a position where the gas present there is to be measured and filled into a container such as a compressed-gas cylinder, which gas may be supplied to intake port 14 from the container.

First, second, and third gas detector 1 (1') of the present embodiment is operated for example in the below mentioned sequence.

Step 1

With first valve 8a closed and second valve Bb opened, piston 5 of syringe 3 is moved from left to right in the drawing. Then, the zero gas is introduced from gas cylinder 9 into sensor unit 7 through second valve 8b and, therein, the zero point of sensor signal 17 is measured. The gas present on the right side of piston 5 of syringe 3 is exhausted to the outside through exhaust port 15b.

Step 2

With first valve 8a opened and second valve 8b closed, piston 5 of syringe 3 is moved from right to left in the drawing. At this time, the test gas is introduced from intake port 14 into sensor unit 7 through first valve 8a and, therein, a change at the rise of sensor signal 17 is measured. The test gas introduced in sensor unit 7 as it is is taken into the volume on the right side of piston 5 of syringe 3. With the movement of piston 5, the gas on the left side is exhausted to the outside through exhaust port 15a.

Step 3

With first valve 8a closed and second valve 8b opened, piston 5 of syringe 3 is moved from left to right in the drawing. At this time, the zero gas is introduced from gas cylinder 9 into sensor unit 7 through second valve 8b and, therein, a change at the fall of sensor signal 17 is measured. The gas present on the right side of piston 5 of syringe 3 is exhausted to the outside through exhaust port 15b.

Through the drive as described above, signal waveforms as shown in FIG. 2, for example, can be observed. By taking the waveforms into the data processor and making analysis of the same, accurate identification of the odor of the test gas can be achieved.

FIG. 2 is a principle drawing of the identification performed in the present gas detector, in which are shown signal waveforms obtained by sensors 30a, 30b, and 30c arranged in sensor unit 7 for detecting different gas components. More specifically, against the zero level of sensor signal 17 detected from the zero gas taken in at step 1, changes in electric resistance in each sensor 30a, 30b, and 30c are measured as indicated by A, B, and C. Identification of the odor can be achieved by having these waveforms taken into data processor 11 to be analyzed therein.

FIG. 3 is a principle drawing of the sensor structure for identifying odors in such sensors 30a, 30b, and 30c.

More specifically, sensor 30' has high polymer body 45 with carbon black, for example, dispersed therein and electrodes 46 disposed on both sides of the body. By having high polymer body 45 exposed to the gas introduced into a chamber, the odor component attaches to high polymer body 45 to thereby swell it and change its electric resistance value. Hence, the change in resistance value is measured by a measuring circuit through wires and the result is measured as the signal wave charts as shown in FIG. 2.

Now, with reference to concrete examples shown in FIG. 4A to FIG. 8, structure and function of sensors within sensor unit 7 in gas detector 1 (1') according to the present embodiment will be described.

Figure 4A:
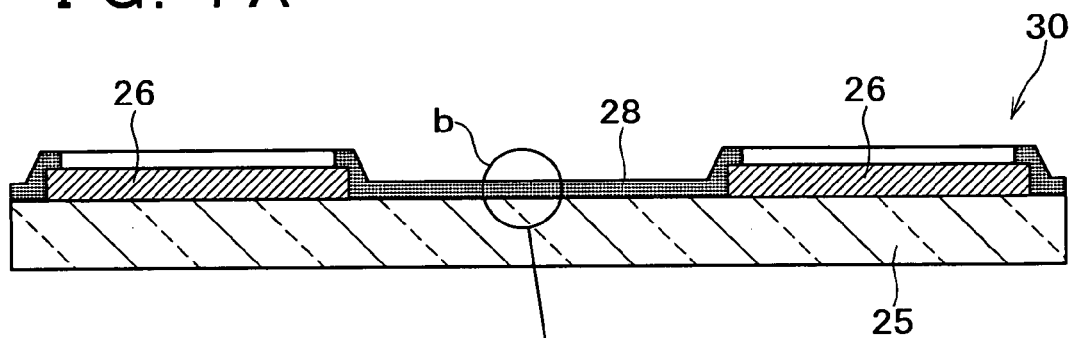
FIG. 4A to FIG. 4C are drawings showing structure of the sensor of the same gas detector.

Sensor 30, as shown in FIG. 4A, is formed of glass substrate (of a thickness, for example, of 300 μm or so) 25 with electrodes 26 disposed on both sides thereof and thin film 28 of the sensor material provided all over the surface except the top plane of electrode 26. Glass substrate 25 is a supporting member for supporting thereon thin film 28 of the sensor material and electrodes 26. As the material of the substrate, a silicon substrate or plastic substrate with an oxide film formed thereon may also be used. Electrodes 26 constitute electric contacts between sensor-material thin film 28 and external wirings and the same are formed by lift-off patterning a vaporized film with a thickness of Ti/Au=50 nm/200 nm.

Figure 4B:
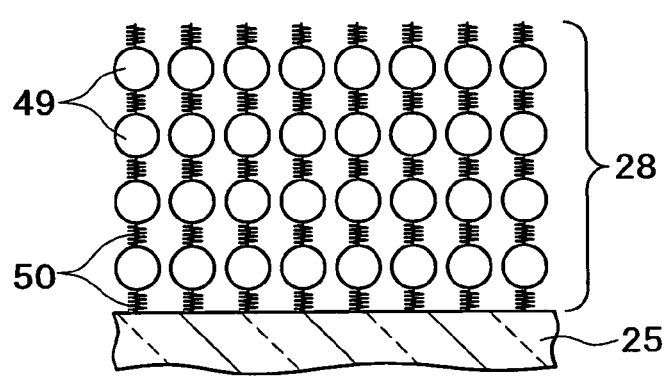
Figure 4C:
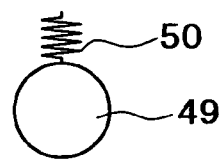

Sensor-material thin film 28 is a thin film whose electric resistance varies when it adsorbs an odorous molecule of a specific kind and it has a laminar structure, as shown in FIG. 4B and FIG. 4C which are enlarged sectional views of portion b in FIG. 4A, in which metal fine particles 49 (for example, Au particles of around ϕ=4 nm) are mutually bonded by linker molecules 50. Linker molecule is an organic molecule having, at least at two positions, a functional group (for example, —SH group against Au particles) forming coordinate bond with metal fine particles. For example, 1,9-nonane dithiol or Biphenyl dithiol is used for the same.

Figure 5A:
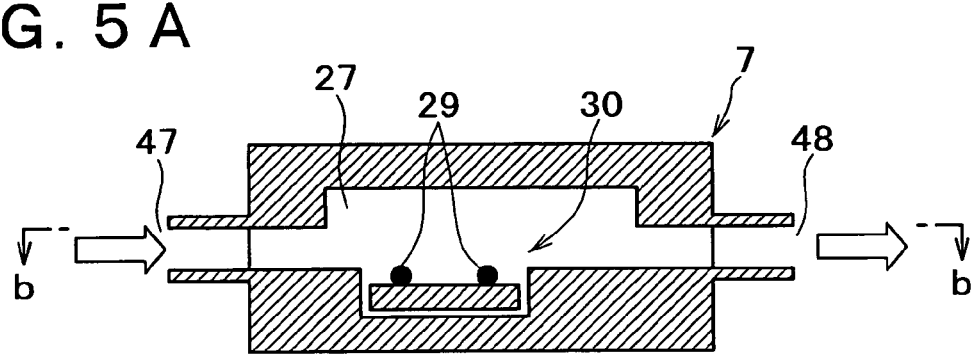

FIG. 5A is a schematic sectional view of sensor unit 7 containing sensors 30 as described above and FIG. 5B is a sectional view taken along line b—b of FIG. 5A.

Figure 5B:
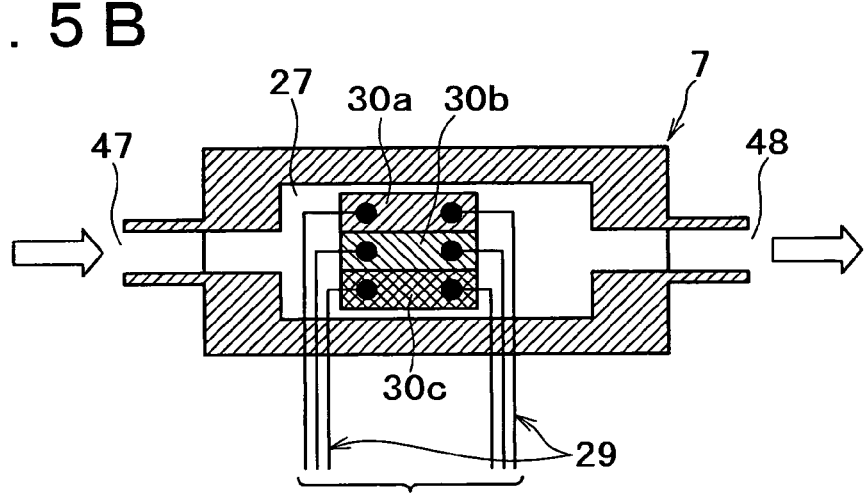

There are disposed, for example, three kinds of sensors 30a, 30b, and 30c within sensor unit 7 as shown in FIG. 5B, and these sensors 30a, 30b, and 30c are housed in hermetically sealed sensor chamber 27 (made for example of TEFLON (trademark)). Any number, from one to many, of kinds of sensors 30 may be used.

Those contained sensors 30a, 30b, and 30c are exposed to the gas while it is introduced through inlet port 47 provided in sensor chamber 27 and exhausted through outlet port 48, whereby their electric resistance values are changed. Changes in the electric resistance of the sensors are each measured by a sensor measuring circuit through electric wirings 29 connected to sensors 30a, 30b, and 30c.

Figure 6:
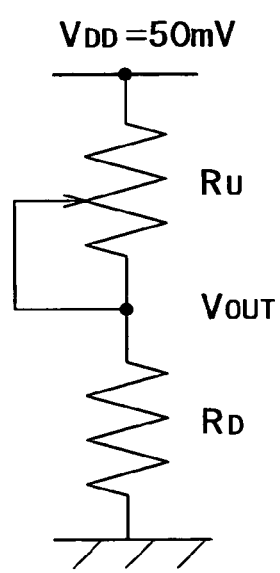
FIG. 6 is a measuring circuit diagram of the same sensor.

FIG. 6 is a drawing showing the measuring circuit for each individual sensor. The value of relative difference may be obtained by using this circuit for measuring divided voltage $V_{OUT}$ on reference resistance $R_U$. In this case, relation between divided voltage $V_{OUT}$ and $R_D$ is expressed as:

$$V_{OUT} = V_{DD} \times R_D / R_U + R_D, \text{ where } V_{DD}, R_U \text{ are constants.}$$

Namely, the value of relative difference of $R_D$ can be known by measuring $V_{OUT}$. When this circuit is used, since the measured voltage falls within a predetermined range $(0-V_{DD})$ regardless of the resistance value of the sensor, the need for changing the measuring range can be eliminated and hence such an advantage is obtained that simplification and speedup of the voltage measuring circuit can be attained.

Reference resistance $R_U$ is preferably set up such that its resistance value is substantially equal to that of sensor resistance $R_D$. At this time, maximum voltage sensitivity can be obtained. $V_{DD}$ is a fixed voltage for generating $V_{OUT}$ and its value is set up with such factors as withstanding voltage and life of the sensor, measurement accuracy of $V_{OUT}$, and produced noise taken into consideration (for example, at 50–200 mV).

Figure 7:
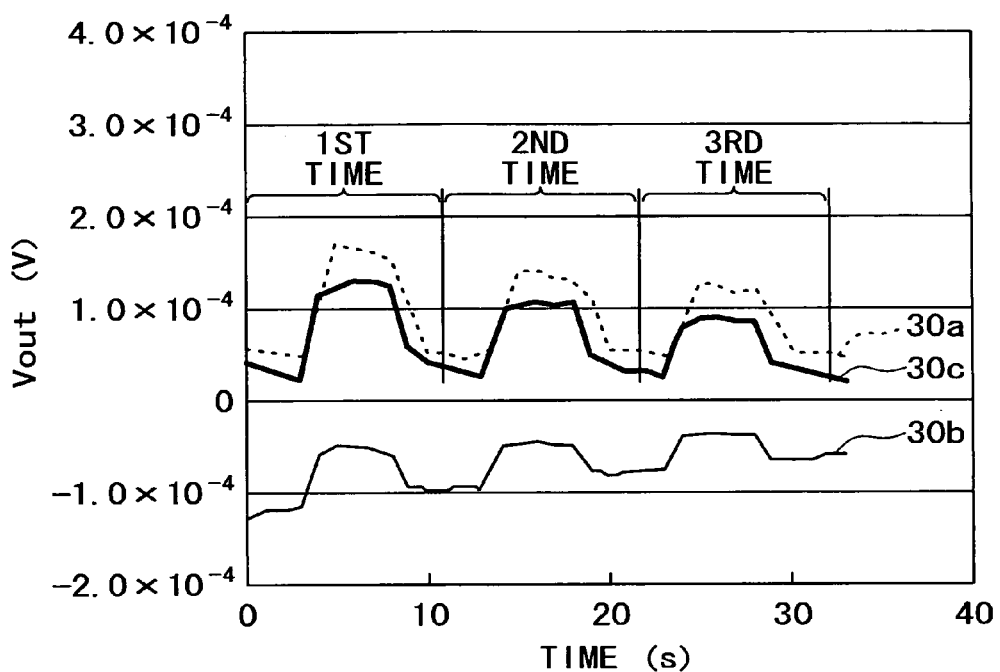
FIG. 7 is a graph showing a concrete example of measurements made by the same gas detector.
Figure 8:
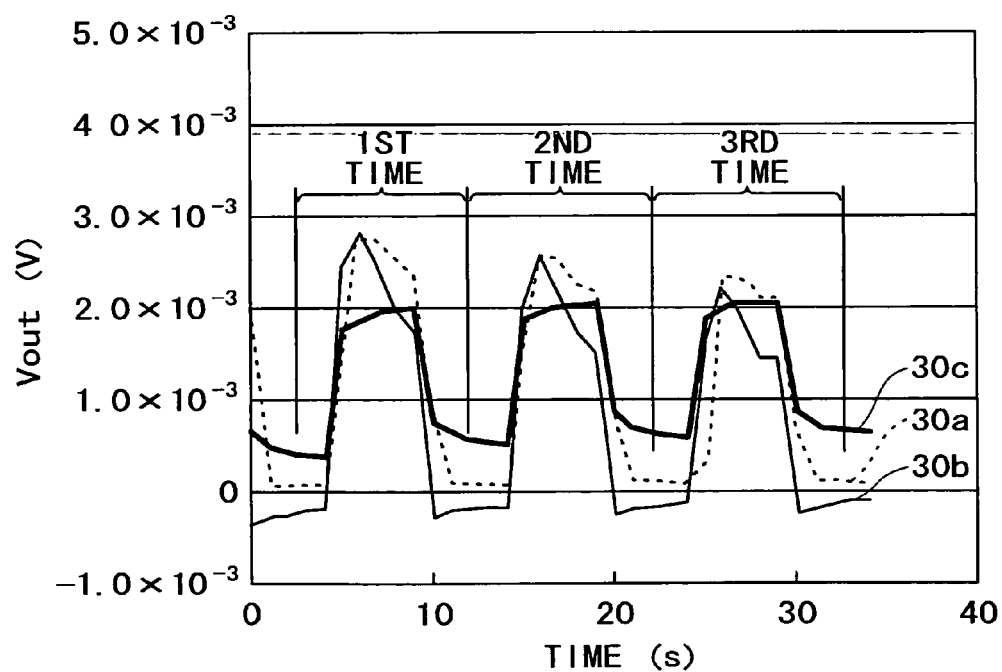
FIG. 8 is a graph showing another concrete example of measurements made by the same gas detector.

FIG. 7 and FIG. 8 show examples of measurement by gas detector 1 of the present embodiment and there are shown graphs of actual measurement of signal waveforms in this measurement. For example, FIG. 7 is an example of measurement on coffee bean and FIG. 8 is an example of measurement on whiskey, and both of which are results of measurement of signal waveforms measured with the same sensor array.

Since, as described above, sensor unit 7 is formed of three different sensors 30a, 30b, and 30b, it is found that response waveforms and signal amplitudes from the different sensors are different between coffee bean and whiskey. Thus, from differences in the signal pattern, coffee and whiskey can be identified.

In such sensors, a component responding more strongly to a sensor differs from sensor to sensor. Therefore, for example, a sensor responding more strongly to a hydrophilic molecule, a sensor responding more strongly to a hydrophobic molecule, and the like may be arranged therein so that performances of sensors composing a sensor array can be changed in accordance with the composition of components considered to be contained in the subject of measurement.

In any of the measured waveforms, the height of the waveform is becoming smaller with the passage of time and, thereby, changes in the waveform amplitude can be observed (each sensor of FIG. 7 and FIG. 8). Further, shifts in position of the zero level in each sensor can be observed (for example, in FIG. 7, the position of zero level is decreasing in sensors 30a and 30c and it is increasing in sensor 30b). The phenomena are caused by deterioration of the sensor function due to attachment to the surface of the sensor material of odorous molecules contained in coffee bean and whiskey, hydrophilic molecules considered to be largely contained in coffee bean and whiskey, and the like. Accordingly, by introducing the zero gas and the test gas alternately into the sensor unit, the differences in signal strength between the zero gas and the test gas can be measured in terms of relative difference while the zero level of the sensor is being adjusted.

By the use of the gas detector according to the present embodiment as described above, the gas present at a position desired to be measured can be measured and, in addition, with attention paid to an object, the kind, quantity, concentration, and the like of particular components contained in the atmosphere surrounding the object can be measured simply and accurately.

According to the present embodiment, first gas detector 1 has gas cylinder 9 containing the zero gas as the reference gas installed within enclosure 2 and adapted to introduce an ambient gas as the test gas through intake port 14 to thereby make the measurement. Hence, those gases are alternately introduced into the sensor and the measured results are relatively compared at each measurement and, thereby, accurate measurement of the odor in the ambient gas can be achieved, and, in addition, operability is enhanced, and gas detector 1 can be moved to a place where measurement is to be made so that measurement on the spot is enabled. Further, when the test gas is supplied from a cylinder containing a separately sampled gas, measurement can be performed with the apparatus fixed in another position than the spot. Further, it is possible to install syringe 3 for intake and exhaust of gas within enclosure 2 and, thereby, quantification of taken-in and exhausted gases, as well as low-noise operation, can be attained.

Further, second gas detector 1' can introduce an ambient gas outside the enclosure as the test gas for measurement. This test gas and the zero gas can be introduced into the sensor alternately and the measured results can be relatively compared each time of measurement to thereby attain accurate measurement of the odor of the test gas. Further, since the intake and exhaust of these gases are performed by use of syringe 3, the intake and exhaust of gases can be quantified and operation can be performed with low noise. Further, operability of the apparatus is enhanced and it is also made possible to incorporate zero gas cylinder 9 in the enclosure as the supply source of zero gas. By having zero gas cylinder 9 internally installed, it becomes possible to move apparatus 1 to a spot where measurement is desired to be made and make measurement at the spot and, further, by sampling the test gas only and supplying it to the apparatus, it is possible to make measurement at a different place from the spot.

Second Embodiment

Figure 9:
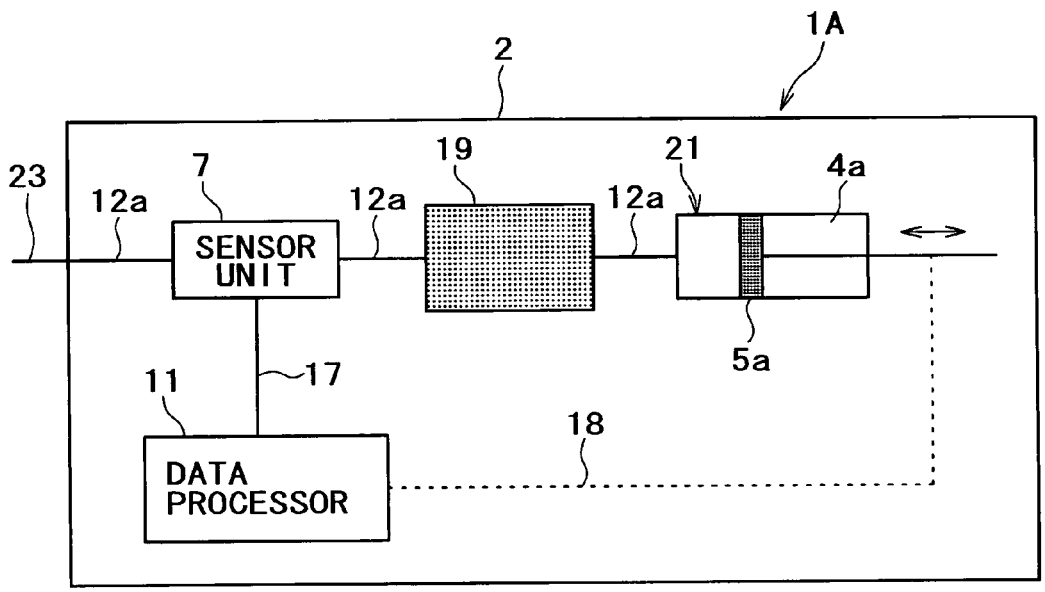
FIG. 9 is a schematic block diagram of a gas detector according to a second embodiment of the present invention.

FIG. 9 shows a schematic block diagram of gas detector 1A according to the present embodiment.

This gas detector 1A, like the above-described first embodiment, is adapted such that an ambient gas is taken into the enclosure as the test gas. It is configured to be different from the first embodiment in the source of supply of the reference gas, the cylinder mechanism, and pipes and valves accessory thereto. Otherwise, it is configured the same as embodiment 1 and it functions equally to the first and second gas detectors in the first embodiment. Such designs are applicable to the above-described first and second gas detectors.

As the mechanism for intake/exhaust of gas, syringe 21 made up of cylinder 4a and piston 5a for taking in, or exhausting, gas on one and the same side is installed in enclosure 2. As the source of supply of the reference gas, it is arranged such that the test gas after its use is purified in purifier 19 and turned into the reference gas.

More specifically, the outside air taken in from intake/exhaust port 23 through piping 12a is subjected to measurement for data on the test gas in sensor unit 7 and, thereafter, the gas is purified in purifier 19 and temporarily stored into cylinder 4a of syringe 21. When the gas is exhausted therefrom, it is purified again in purifier 19 to be turned into a gas for reference and this gas is supplied to sensor unit 7 as the reference gas. Thus, the test gas and the reference gas are alternately introduced into sensor unit 7 and the results of measurement on gases in sensor unit 7 are relatively compared, so that accurate measurement of the test gas is attained, and by use of the intake/exhaust mechanism formed of syringe 21, intake and exhaust of the gas can be quantified and a gas detector producing low noise and being small in size can be configured to be portable. However, also in this case, measurement can be made with the apparatus fixed in place by a supply of the test gas that is sampled.

As described above, gas detector 1A of the present embodiment purifies the test gas used for odor measurement to reuse the gas as the zero gas. Thereby, valves and parts required for changing over to the zero gas can be reduced and the apparatus can be simplified in structure. Thus, a small-sized odor identifier suitable for portable use and built-in arrangement can be provided.

Also in this embodiment, a sensor of the type hitherto in use can be used. Purifier 19 is an apparatus for eliminating moisture and odorous molecule from the test gas. It is, for example, a filter unit having containers, each thereof containing silica gel, activated carbon, and various catalysts, arranged such that the gas is passed through the individual containers in turn. Syringe 21 is made up of cylinder 4a, piston 5a, and a piston driver, in which piston 5a makes reciprocating motion in accordance with control signal 18 from data processor 11. Accordingly, there is no need for valve change-over.

When piston 5a takes in the test gas, the environmental gas is taken in through intake/exhaust port 23 and sent to sensor unit 7. The test gas sent to sensor unit 7 gives rise to changes in sensor signal 17 characteristic of the test gas and the data is measured in data processor 11. In succession thereto, this gas is sent to purifier 19 where odorous molecule and moisture contained in the gas are eliminated. The thus purified gas is temporarily stored into cylinder 4a of syringe 21.

Then, piston 5a forces out the purified gas stored in syringe 21. At this time, the purified gas stored in cylinder 4a is sent to sensor unit 7 through purifier 19 again. Then, the gas sent to sensor unit 7 has been turned into a zero gas by two times of purification and, therefore, signal patterns characteristic of the test gas can be obtained by comparison of the response to the zero gas of sensor unit 7 with the response to the test gas and, thereby, accurate identification of the test gas can be attained.

Since this gas detector 1A internally generates a zero gas by purification of the test gas, accurate identification of the test gas can be made even if the test gas is such that is widely distributed in the environment surrounding gas detector 1A.

Figure 10:
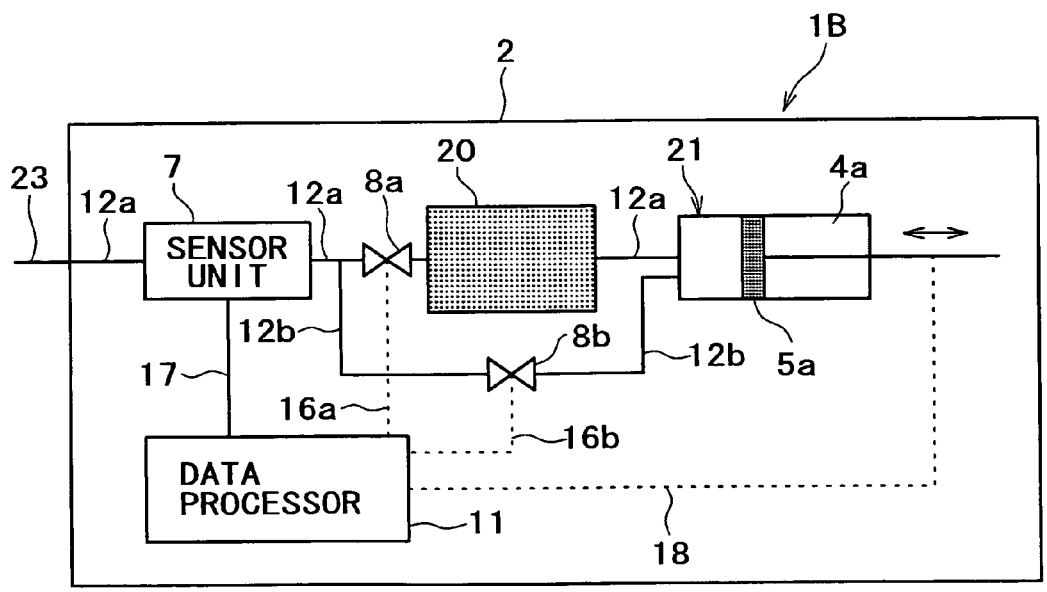
FIG. 10 is a schematic block diagram of a modification of the gas detector according to the same second embodiment.

FIG. 10 is a schematic block diagram of gas detector 1B according to a modification of the second embodiment.

More specifically, the purification capacity of purifier 20 can be enhanced by material contained therein, internal structure, and the like, and it is possible to generate a zero gas as the reference gas even only by one time of filtration. Accordingly, purifier 20 with a high purification capacity is disposed and necessary piping 12b and valves 8a, 8b are disposed in different arrangement from that in FIG. 9. Further, this apparatus, like the apparatus shown in FIG. 9, can be applied to the above-described first and second gas detectors.

Since gas detector 1B is capable of generating a reference gas by one time of filtration with use of purifier 20, valve 8a is opened and valve 8b is closed at the time of intake by syringe 21, so that the test gas taken in is passed through sensor unit 7 and purifier 20 and the generated reference gas is temporarily stored into cylinder 4a of syringe 21. When the same is exhausted, valve 8a is closed and valve 8b is opened and the reference gas is supplied to sensor unit 7 through piping 12b.

Figure 11:
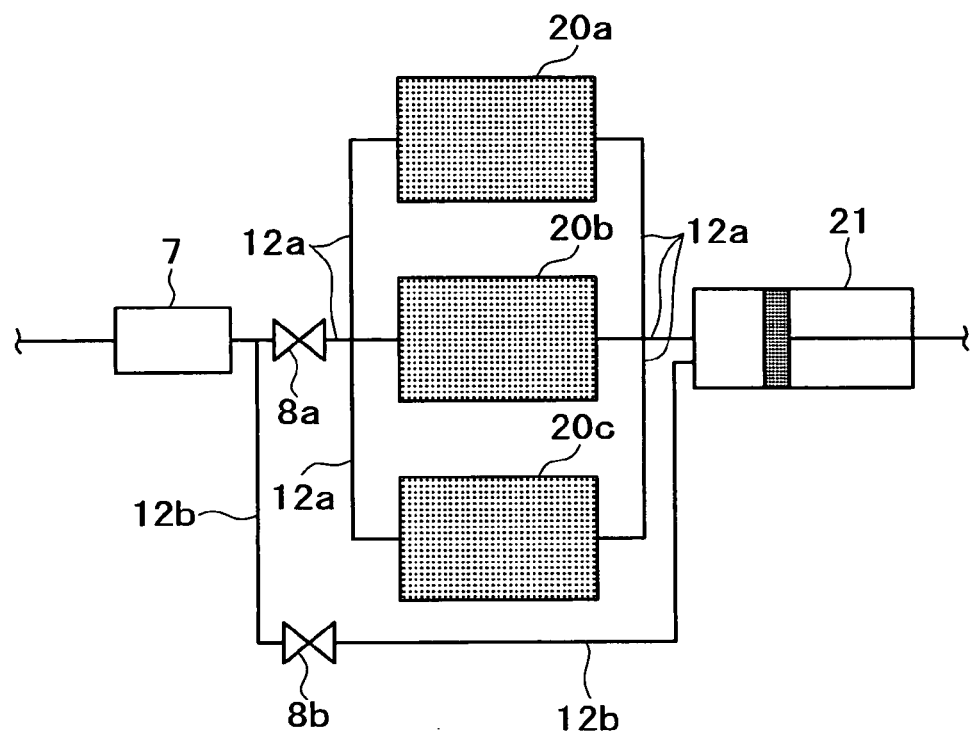
FIG. 11 is a schematic block diagram showing another example of a gas purifier unit of the gas detector according to the same second embodiment.
Figure 12:
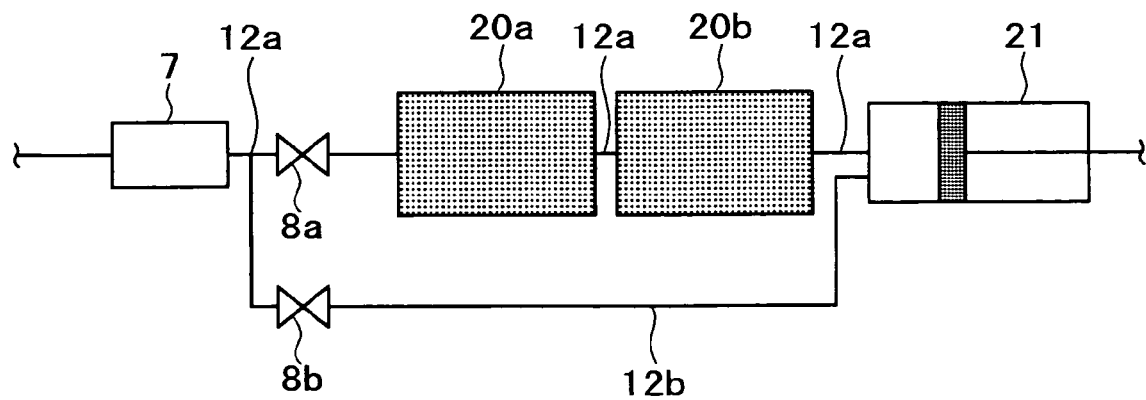
FIG. 12 is a schematic block diagram showing a further example of a gas purifier unit of the gas detector according to the same second embodiment.

FIG. 11 and FIG. 12 are drawings showing other examples of the filter configuration of purifier 20 in gas detector 1B. One example has as shown in FIG. 11 a plurality of purifiers 20a, 20b, and 20c arranged in parallel. What is shown in FIG. 12 has purifiers 20a and 20b (20c may be added thereto), similar to those mentioned above, arranged in series. Both examples can exhibit the same purification capacity as that of FIG. 11.

According to the present embodiment, the ambient gas of enclosure 2 can be introduced for measurement of the odor thereof. Since, in addition, the reference gas can be internally generated by purifying the test gas taken in from the outside by use of purifier 19 (or 20) provided within enclosure 2, the test gas and the reference gas can be alternately introduced into the sensor so that accurate measurement can be made and, further, it is made possible to carry gas detector 1A (or 1B) to a place where measurement is to be made to attain measurement on the spot and, in addition, when the test gas is supplied from a gas cylinder, measurement can be made with the apparatus fixed in another place than the spot.

Although a syringe is used as the intake/exhaust unit in the above-described examples, the same may be replaced with a bellows pump. Even if a bellows pump is used, the same low-noise characteristic and reduction in size can be obtained as when the syringe is used.

Figure 13:
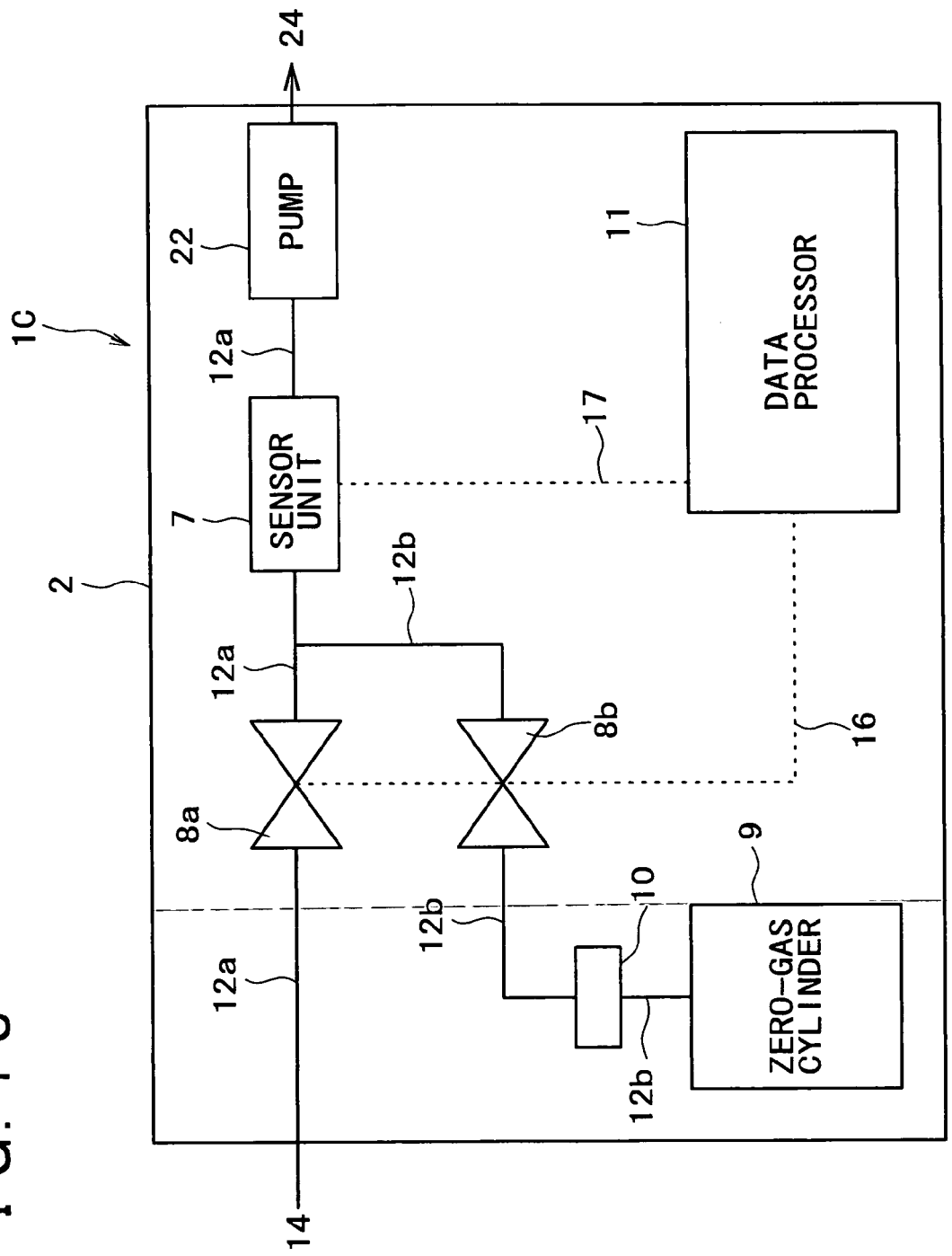
FIG. 13 is a schematic block diagram showing a modification of the gas detector according to the first embodiment of the present invention.
Figure 14:
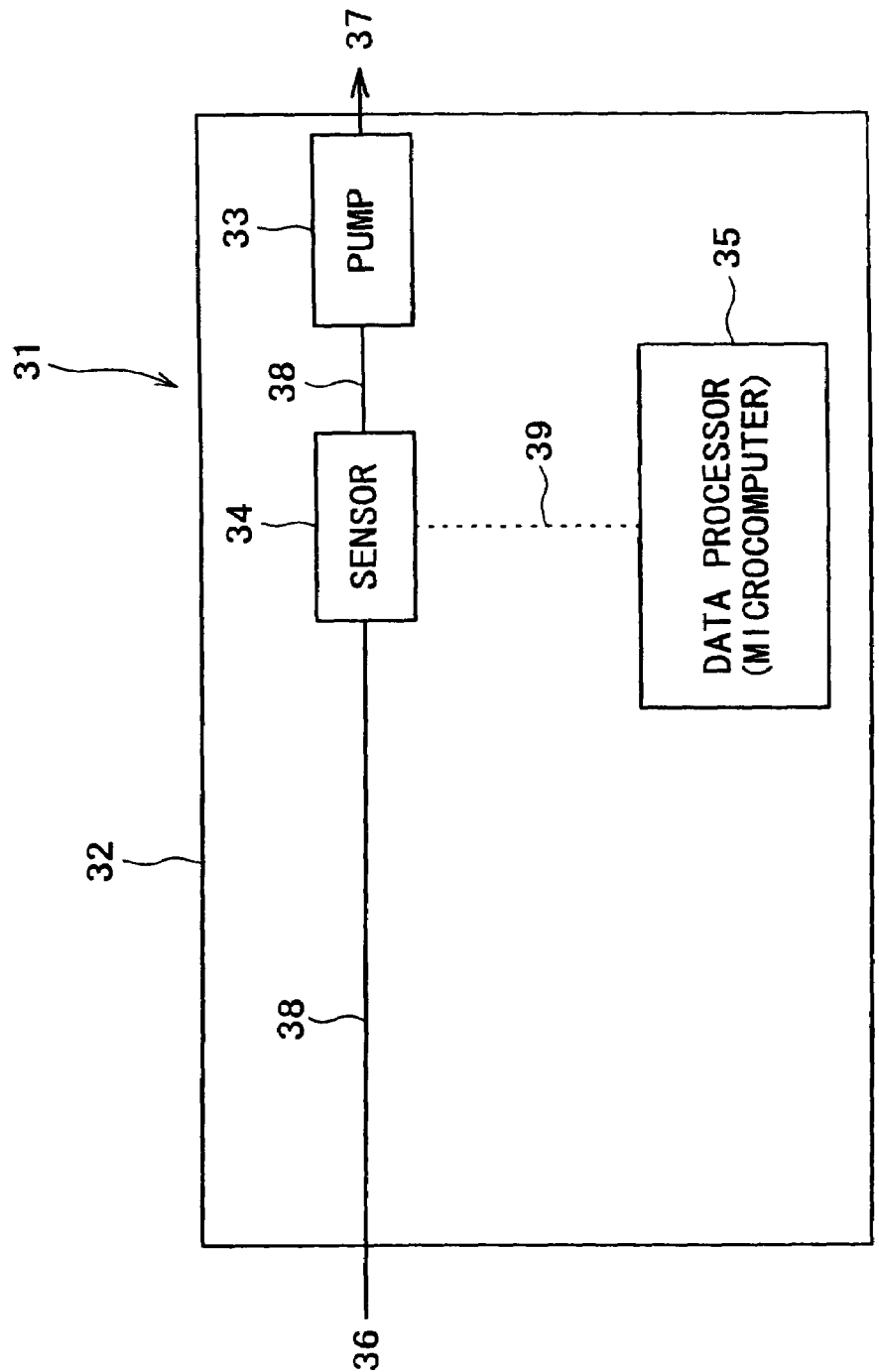
FIG. 14 is a schematic block diagram of a gas detector in a conventional example.
Figure 15:
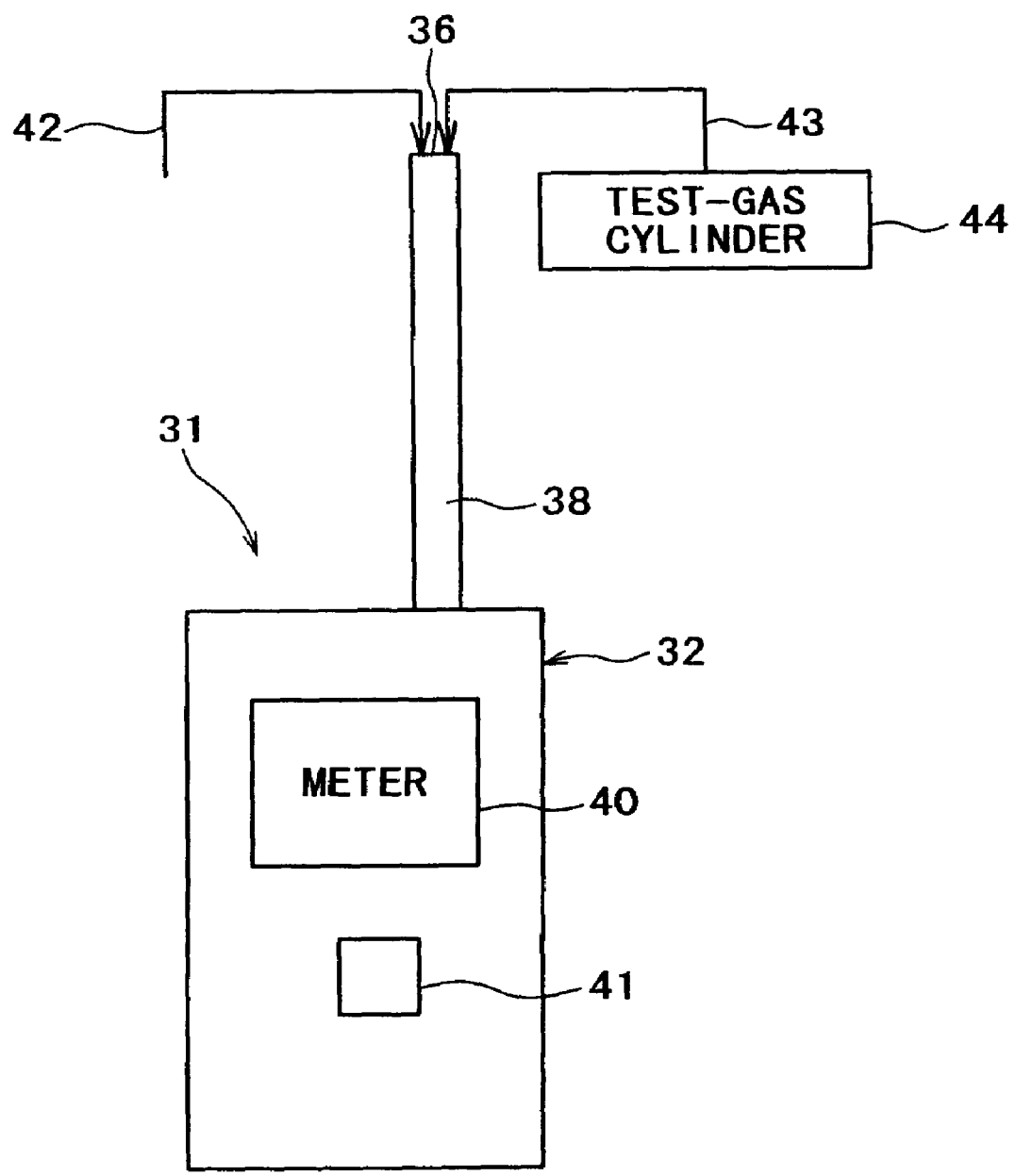
FIG. 15 is a schematic outside view of the same gas detector.

FIG. 13 is a schematic block diagram showing gas detector 1C as a modified example of the first embodiment, which, like the first embodiment, can be applied to the first and second gas detectors.

More specifically, this gas detector 1C, as shown in FIG. 13, is provided with a pump, as the gas intake/exhaust unit, similar to those in conventional examples. Since, otherwise, it is configured the same as the first embodiment, by operating it the same as the first embodiment is operated, sufficient performance can be provided. In addition, since it can be arranged to be portable, the apparatus can be carried to a spot where measurement is to be made and to make measurement at the spot. Further, by arranging such that the test gas is supplied from a gas cylinder, measurement at a spot can be made while the apparatus is fixed in a place other than the spot.

According to The above-described embodiments, since the zero gas is supplied from a source installed within the enclosure or generated within the enclosure with use of a purifier, it is not restricted by the place of installation and enabled to identify an odor of the environment surrounding the odor identifier.

Accordingly, when the apparatus is incorporated in a robot, for example, the robot, by analyzing the odor in the surroundings of it, is enabled for example to detect a fire occurring in a separate room of a house or in the neighborhood, doneness of cooking, returning home of a family member, a forcible entry, or the like. By carrying the apparatus to a street, a wood, and the seaside, identification of odors in their environments can be attained.

Further, by the use of a syringe or a bellows pump as the intake/exhaust mechanism, noises generated by the intake/exhaust operation can be suppressed and a small-sized odor identifier suited for portable and built-in design can be realized.

Further, by purifying a test gas used for measurement by the sensor and storing the gas, and by reusing it as a zero gas, number of components, such as valves, required for switching between the zero gas and the test gas can be reduced and the overall size of the apparatus can be made still smaller.

The above-described embodiments can be modified without departing the technical spirit of the present invention.

For example, as to the test gas, while the apparatus can be carried to a spot where measurement is to be made so that the environmental gas at the spot is measured by taking in the test gas at the spot, it can also measure the test gas sampled and put into a container such as a pressure gas cylinder, with the apparatus fixed in a separate place.

Further, the first gas detector is defined to have the zero gas cylinder installed internally while it is allowed to use a syringe as the intake/exhaust mechanism of gas, whereas the second gas detector is defined to have a syringe installed as the gas intake/exhaust mechanism and, for the zero gas, it is allowed to have a zero gas cylinder installed therein. However, either of the first and second gas detectors may use both the zero gas cylinder and the syringe in combination.

Further, as the intake/exhaust unit of gas, an intake/exhaust unit employing a piezoelectric device or another intake/exhaust unit may be used instead of the above-described syringe, pump, or bellows pump.

Although the embodiments have been described to be for use in the identification of an odor of a test gas, they can also be used for measurement of kind, quantity, concentration, or physical-property value of a gas.

Further, as to structure, arrangement, and the like of various parts of the apparatuses shown in the embodiments, they can be practiced suitably in other ways than have been described in the embodiments. The above-described gas detector can be incorporated in a robot apparatus driven in an autonomous manner.

According to the first and third gas detectors of the present invention, the source of supply of the reference gas is installed within the enclosure and the test gas is taken in from outside the enclosure, or the source of supply of the reference gas and the sensor are integrated in one body. Therefore, an ambient gas at a region to be tested can be taken in from outside the enclosure as the test gas to thereby measure the ambient gas. Further, a test gas and a reference gas can be alternately introduced into the sensor incorporated in the enclosure and results of measurement on these gases can be relatively compared at each time of measurement to thereby make accurate measurement on the test gas. Since, at this time, the reference gas is introduced from a source of supply of the reference gas installed within the enclosure, the overall size of the apparatus can be arranged to be compact as compared with the case where the source of supply of the reference gas is installed outside, and, in addition, it becomes easy to arrange the whole of the apparatus together with the source of supply of the reference gas to be movable to a desired place.

Further, according to the second gas detector of the present invention, the reference gas from the reference gas supply source or the reference gas from outside the enclosure can be introduced into the sensor through reciprocating motion of the piston of the cylinder mechanism, and hence an ambient gas can be measured by introducing the ambient gas as the test gas from outside the enclosure. Further, measurement of the test gas can be performed accurately by alternately introducing the test gas and the reference gas from the reference gas supply source into the sensor and relatively comparing the results of the measurement at each time of measurement. Furthermore, since these gases are taken in and exhausted by the reciprocating motion of the piston in the cylinder, amounts of intake and exhaust of the gases can be quantified and it can be attained to provide a low noise and small-sized gas detector.

The invention claimed is:

1. A gas detector comprising a sensor configured to alternately introduce a reference gas and a test gas into the sensor, within an enclosure for detecting a particular component contained in the test gas, the gas detector characterized by that a source of supply of the reference gas is installed within the enclosure and the test gas is taken in from outside the enclosure, said gas detector further comprising:

an intake/exhaust mechanism for taking in or exhausting a gas by expansion or contraction of inner space thereof;

a passage of the reference gas or the test gas communicating with the intake/exhaust mechanism;

a source of supply of the reference gas for use in determination of a zero level of the test gas at the detection;

the sensor for use in measurement on the reference gas and the test gas; and a controller for performing at least one of processing of output data from the sensor and controlling of operation of each unit;

wherein the test gas or the reference gas is supplied to the sensor by intake/exhaust motion of the intake/exhaust mechanism, and a particular component in the test gas is identified in accordance with strength of a measured signal;

wherein the reference gas or the test gas is introduced into the sensor by reciprocating motion of a piston of a cylinder mechanism formed of the piston and the cylinder in combination;

wherein, when a gas is taken in, a one-way valve for allowing the gas to flow only in one direction from the sensor to the cylinder mechanism is used and, when the gas is exhausted, another one-way valve for allowing the gas to flow only in one direction from the cylinder mechanism to an exhaust port is used.

2. The gas detector according to claim 1, wherein the one-way valve for gas intake is connected between the sensor and one each of two chambers of the cylinder mechanism partitioned by the piston.

3. The gas detector according to claim 2, wherein one side of the two chambers of the cylinder mechanism is connected by a one-way valve each with the sensor and the exhaust port and the other side is connected by a one-way valve each with the sensor and the exhaust port, while each of the one-way valves connecting the sensor with the cylinder mechanism opens and closes to cause the gas to flow only from the sensor to the cylinder mechanism and each of the one-way valves connecting the cylinder mechanism with the exhaust ports opens and closes to cause the gas to flow only from the cylinder mechanism to the exhaust ports, such that gasses are ceaselessly taken into the sensor by a single cylinder mechanism.

4. The gas detector according to claim 3, further comprising:
an intake port for taking in the test gas from outside the enclosure to its interior;
a first valve disposed between the port and the sensor; and
a second valve disposed between the source of supply of the reference gas and the sensor, wherein,
when the piston moves in one direction, the first valve is opened and the test gas is taken into the sensor and, when the piston moves in opposite direction, the second valve is opened and the reference gas is taken into the sensor, so that the reference gas and the test gas are alternately and ceaselessly sent into the sensor by a single cylinder mechanism.

5. A gas detector comprising a sensor configured to alternately introduce a reference gas and a test gas into the sensor, within an enclosure for detecting a particular component contained in the test gas, the gas detector characterized by that a source of supply of the reference gas is installed within the enclosure and the test gas is taken in from outside the enclosure, said gas detector further comprising:
an intake/exhaust mechanism for taking in or exhausting a gas by expansion or contraction of inner space thereof;
a passage of the reference gas or the test gas communicating with the intake/exhaust mechanism;
a source of supply of the reference gas for use in determination of a zero level of the test gas at the detection;
the sensor for use in measurement on the reference gas and the test gas; and
a controller for performing at least one of processing of output data from the sensor and controlling of operation of each unit;
wherein the test gas or the reference gas is supplied to the sensor by intake/exhaust motion of the intake/exhaust mechanism, and a particular component in the test gas is identified in accordance with strength of a measured signal;

wherein the source of supply of the reference gas is a purifying unit of the test gas and the test gas gone through the detection is purified by the purifying unit and then reused as the reference gas;

wherein, when the test gas is taken into a cylinder mechanism through a gas intake port, the gas is subjected to the detection in the sensor and then purified in the purifying unit and stored into the cylinder mechanism and, when the gas is exhausted from the cylinder mechanism, it is passed through the purifying unit again to be purified an turned into the reference gas, and this reference gas is introduced into the sensor.

6. A gas detector comprising a sensor configured to alternately introduce a reference gas and a test gas into the sensor, within an enclosure for detecting a particular component in the test gas, the gas detector wherein a source of supply of the reference gas is connected to the sensor, the test gas is taken in from outside the enclosure, and the reference gas or the test gas is introduced into the sensor by reciprocating motion of a piston of a cylinder mechanism formed of the piston and the cylinder in combination for taking in and exhausting the gas by expansion and contraction of its inner volume;

wherein, when a gas is taken in, a one-way valve for allowing the gas to flow only in one direction from the sensor to the cylinder mechanism is used and, when the gas is exhausted, another one-way valve for allowing the gas to flow only in one direction from the cylinder mechanism to an exhaust port is used.

7. The gas detector according to claim 6, wherein the one-way valve for gas intake is connected between the sensor and one each of two chambers of the cylinder mechanism partitioned by the piston.

8. The gas detector according to claim 7, wherein one side of the two chambers of the cylinder mechanism is connected by a one-way valve each with the sensor and the exhaust port and the other side is connected by a one-way valve each with the sensor and the exhaust port, while each of the one-way valves connecting the sensor with the cylinder mechanism opens and closes to cause the gas to flow only from the sensor to the cylinder mechanism and each of the one-way valves connecting the cylinder mechanism with the exhaust ports opens and closes to cause the gas to flow only from the cylinder mechanism to the exhaust ports, such that gasses are ceaselessly taken into the sensor by a single cylinder mechanism.

9. The gas detector according to claim 8, further comprising:
an intake port for taking in the test gas from outside the enclosure to its interior;
a first valve disposed between the port and the sensor; and
a second valve disposed between the source of supply of the reference gas and the sensor, wherein,
when the piston moves in one direction, the first valve is opened and the test gas is taken into the sensor and, when the piston moves in opposite direction, the second valve is opened and the reference gas is taken into the sensor, so that the reference gas and the test gas are alternately and ceaselessly sent into the sensor by a single cylinder mechanism.

10. A gas detector comprising a sensor configured to alternately introduce a reference gas and a test gas into the sensor, within an enclosure for detecting a particular component in the test gas, the gas detector wherein a source of supply of the reference gas is connected to the sensor, the test gas is taken in from outside the enclosure, and the reference gas or the test gas is introduced into the sensor by reciprocating motion of a piston of a cylinder mechanism formed of the piston and the cylinder in combination for taking in and exhausting the gas by expansion and contraction of its inner volume;

wherein the source of supply of the reference gas is a purifying unit of the test gas and the test gas gone through the detection is purified by the purifying unit and then reused as the reference gas;

wherein, when the test gas is taken into the cylinder mechanism through a gas intake port, the gas is subjected to the detection in the sensor and then purified in the purifying unit and stored into the cylinder mechanism and, when the gas is exhausted from the cylinder mechanism, it is passed through the purifying unit again to be purified and turned into the reference gas, and this reference gas is introduced into the sensor.

* * * * *